US00PP23758P3

(12) United States Plant Patent
Higaki

(10) Patent No.: US PP23,758 P3
(45) Date of Patent: Jul. 23, 2013

(54) *HYDRANGEA* PLANT NAMED 'BC9.2'

(50) Latin Name: ***Hydrangea macrophylla* (Thunb.)**
Varietal Denomination: BC9.2

(75) Inventor: Harrison M. Higaki, San Mateo, CA (US)

(73) Assignee: Bay City Flower Company, Inc., Half Moon Bay, CA (US)

( * ) Notice: Subject to any disclaimer, the term of this patent is extended or adjusted under 35 U.S.C. 154(b) by 80 days.

(21) Appl. No.: 13/135,016

(22) Filed: Jun. 22, 2011

(65) Prior Publication Data

US 2012/0331599 P1 Dec. 27, 2012

(51) Int. Cl.
*A01H 5/00* (2006.01)

(52) U.S. Cl.
USPC ..... Plt./250

(58) Field of Classification Search
USPC ..... Plt./250
See application file for complete search history.

(56) References Cited

PUBLICATIONS

Peppermint Twist. Trademark Electronic Search System (TESS) retrieved on Nov. 15, 2012. Retrieved through the Internet at <http://tess2.uspto.gov/bin/showfield?f=doc&state=4006:puhd2y.4.1> 2 pp.*

* cited by examiner

*Primary Examiner* — June Hwu
(74) *Attorney, Agent, or Firm* — James R. Cypher; Charles R. Cypher

(57) ABSTRACT

A new and distinct cultivar of *Hydrangea macrophylla* (Thunb.) named 'BC9.2' originated as a controlled cross between the unpatented variety 'Sabrina' (the seed parent) and the patented variety 'Glory' (U.S. Plant Pat. No. 20,705). The cultivar 'BC9.2' has predominately white sepals (R.H.S. 155 C (white group) with edges of R.H.S. 63 A (red-purple group). The variety 'BC9.2' has large attractive inflorescences, distinct sepal pigmentation and good commercial characteristics.

4 Drawing Sheets

Botanical classification: *Hydrangea macrophylla* (Thunb.) 'BC9.2'.

Variety denomination: 'BC9.2'.

BACKGROUND OF THE INVENTION

This invention relates to a new and distinct cultivar of the Saxifragaceae family. The botanical name of the plant is *Hydrangea macrophylla* (Thunb.) 'BC9.2'.

The new cultivar originated as a seedling from a controlled cross between the unpatented, commercial variety known as 'Sabrina' which was the seed parent, and the patented, commercial variety 'Glory' which was the pollen parent. 'Glory' is the subject of U.S. Plant Pat. No. 20,705, issued Feb. 2, 2010, to the same inventor.

The variety 'BC9.2' has large attractive inflorescences, a distinctive pigmentation pattern, and desirable characteristics for commercial growing and transport. The seed parent 'Sabrina' is less compact than the new variety. Below is a table comparing the new variety to similar varieties.

TABLE 1

| | New Variety 'BC9.2' | U.S. Plant Pat. No. 20,705 'Glory' | U.S. Plant Pat. No. 15,912 'White Robe' | U.S. Plant Pat. No. 21,668 'Merrit White' |
|---|---|---|---|---|
| Mature Large Leaf size | 11 cm wide × 16 cm long | 14.5 cm × 18.5" long | 16 cm wide × 19 cm long | 15 cm wide × 18 cm long |

TABLE 1-continued

| | New Variety 'BC9.2' | U.S. Plant Pat. No. 20,705 'Glory' | U.S. Plant Pat. No. 15,912 'White Robe' | U.S. Plant Pat. No. 21,668 'Merrit White' |
|---|---|---|---|---|
| Stem strength | Average | Strong | Strong | Strong |
| Sepal Pigmentation | Both sides of sepals are R.H.S. 155 C (white group) with edges of R.H.S. 63 A (red-purple group). | Upper side of sepals is R.H.S. 155 D (white group); Underside of sepals is R.H.S. 155 D (white group) | Both sides of sepals are R.H.S. 155 D (white group). | Both sides of sepals are R.H.S. 155 D (white group). |
| Sepalous Floret Size | 50 mm | 45 mm diameter | 65 mm to 75 mm | 60 mm to 70 mm |

The new cultivar 'BC9.2' has been successfully asexually reproduced under controlled environmental conditions at a nursery in Half Moon Bay, Calif. under the direction of the inventor with its distinguishing characteristics remaining stable.

Asexual reproduction was first accomplished when vegetative cuttings were taken from the initially selected plant. Examination of asexually reproduced, successive generations grown in Half Moon Bay, Calif. show that the combination of characteristics as herein disclosed for 'BC9.2' remains firmly fixed through three generations.

DESCRIPTION OF THE DRAWINGS

The accompanying drawings consist of color photographs that show the typical plant form, including the inflorescence, foliage, and sepals.

DESCRIPTION OF THE NEW PLANT

Figure 1:
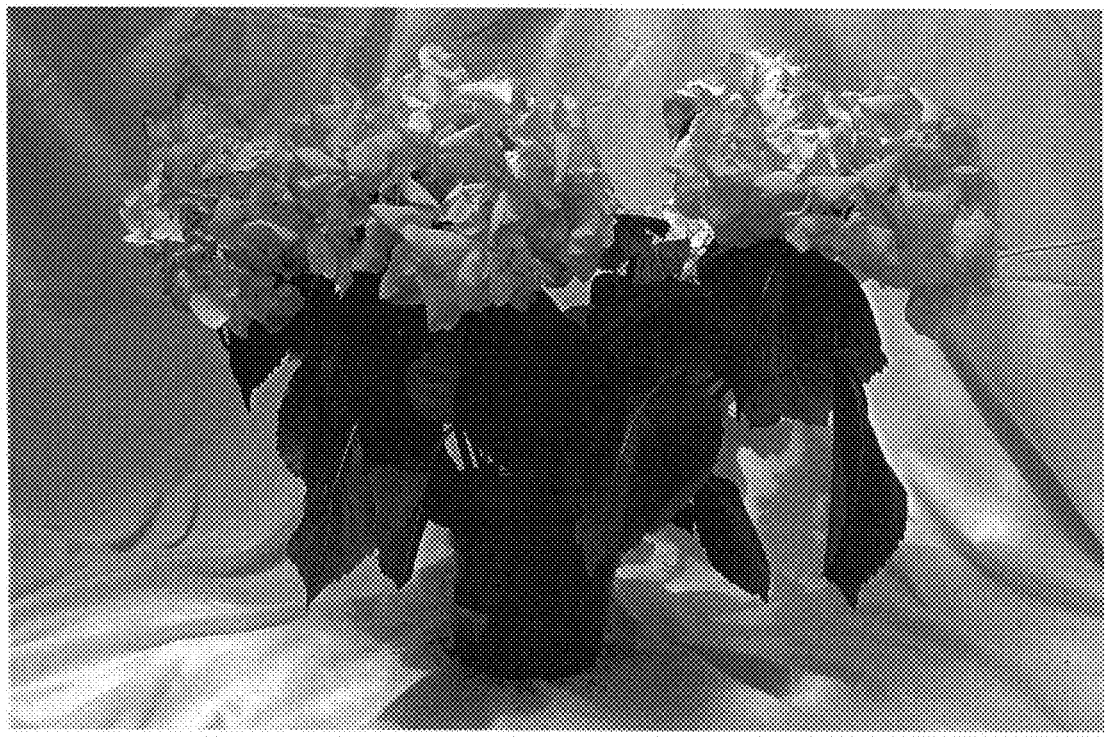
FIG. 1 is a view of the entire plant showing its form, growth habit, dark green foliage, inflorescence, and the color of its sepals.
Figure 2:
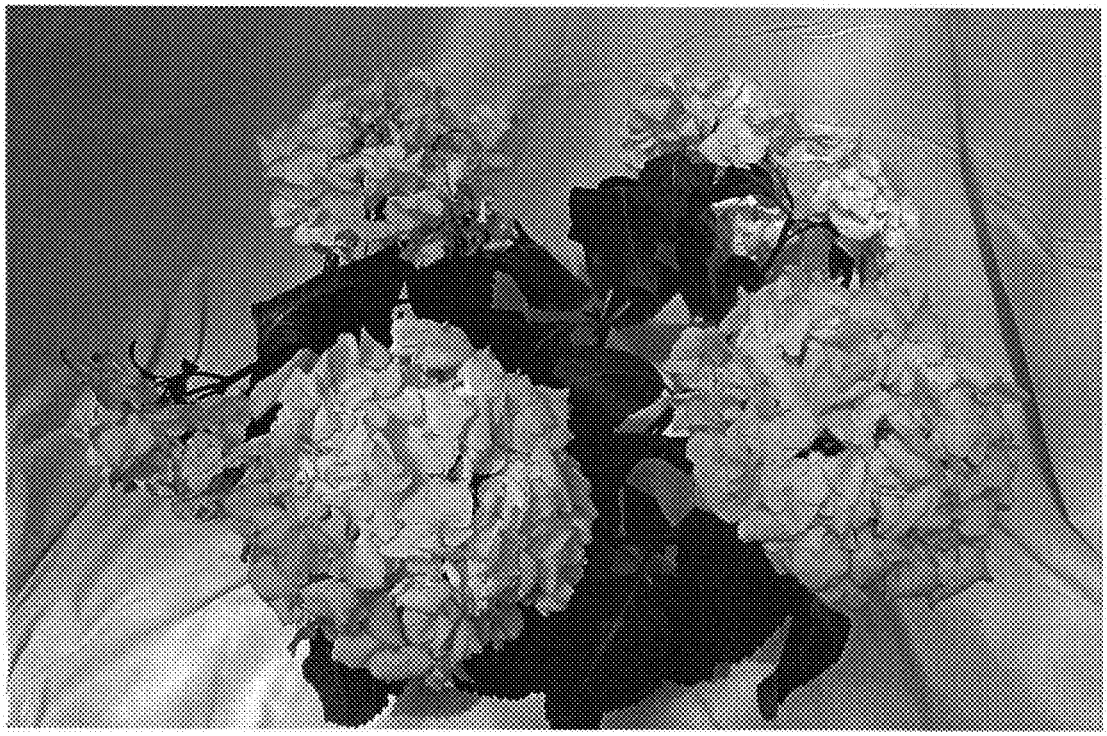
FIG. 2 is a view of the entire plant showing its form, growth habit, dark green foliage, inflorescence, and the color of its sepals.
Figure 3:
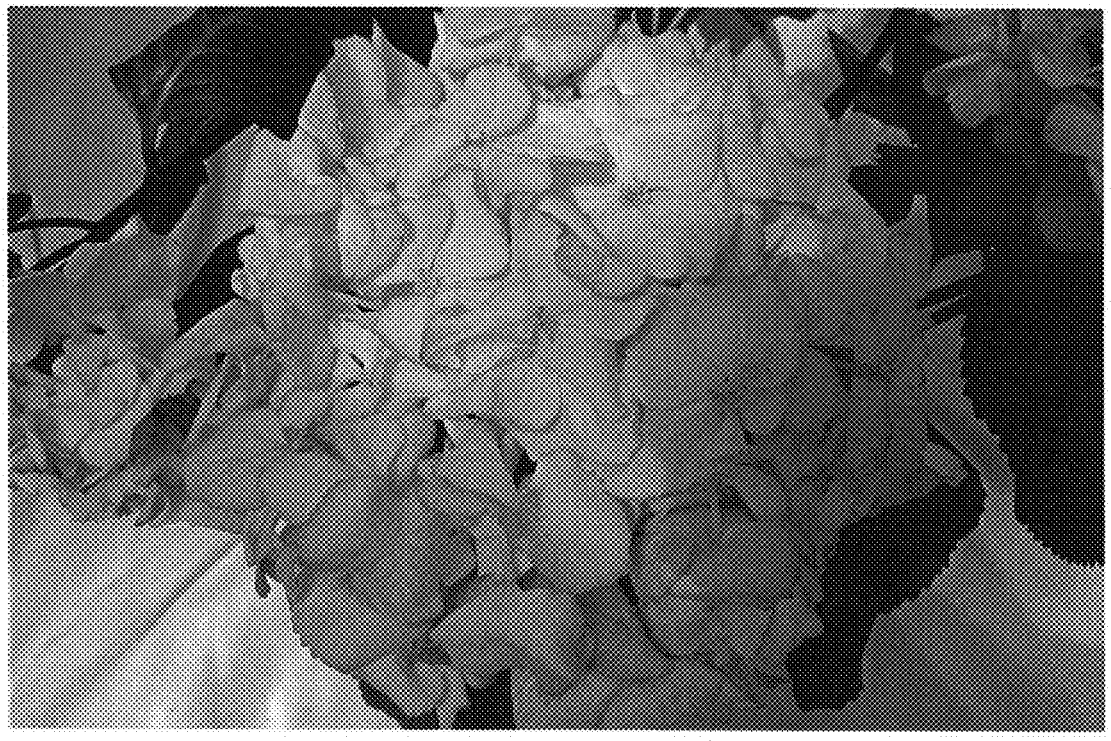
FIG. 3 is a close-up view of the upperside of a panicle of the new variety, showing opened and unopened sepalous florets.
Figure 4:
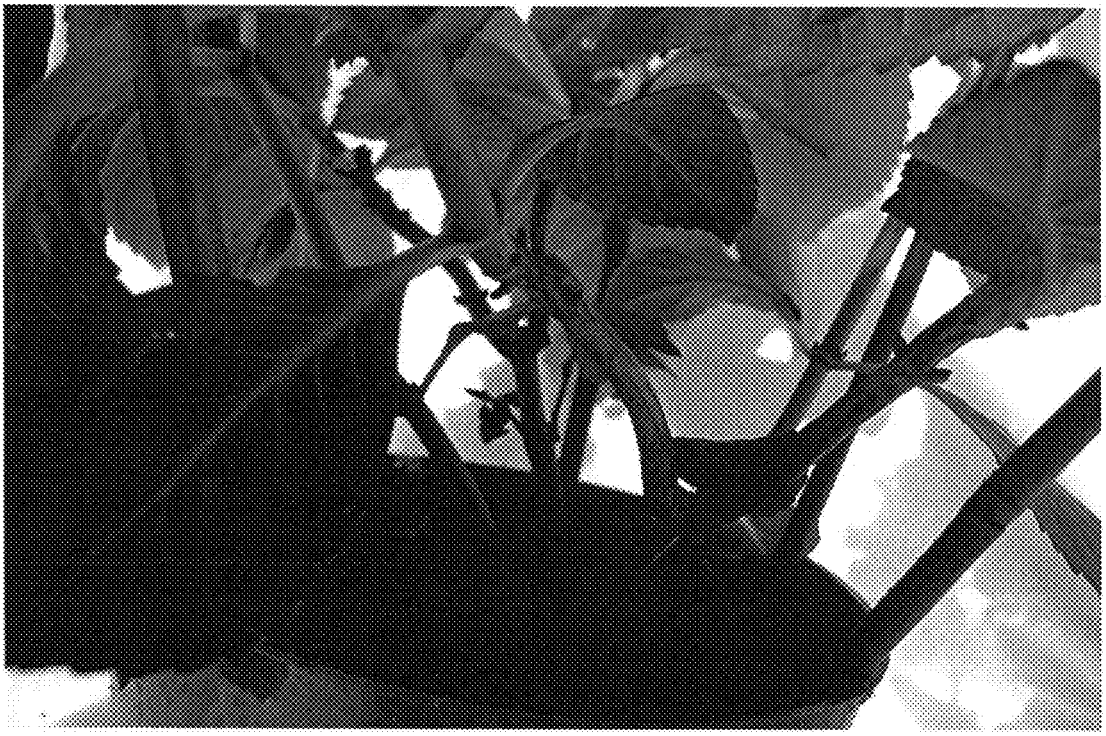
FIG. 4 is a close-up view of the base of the stem.
Figure 5:
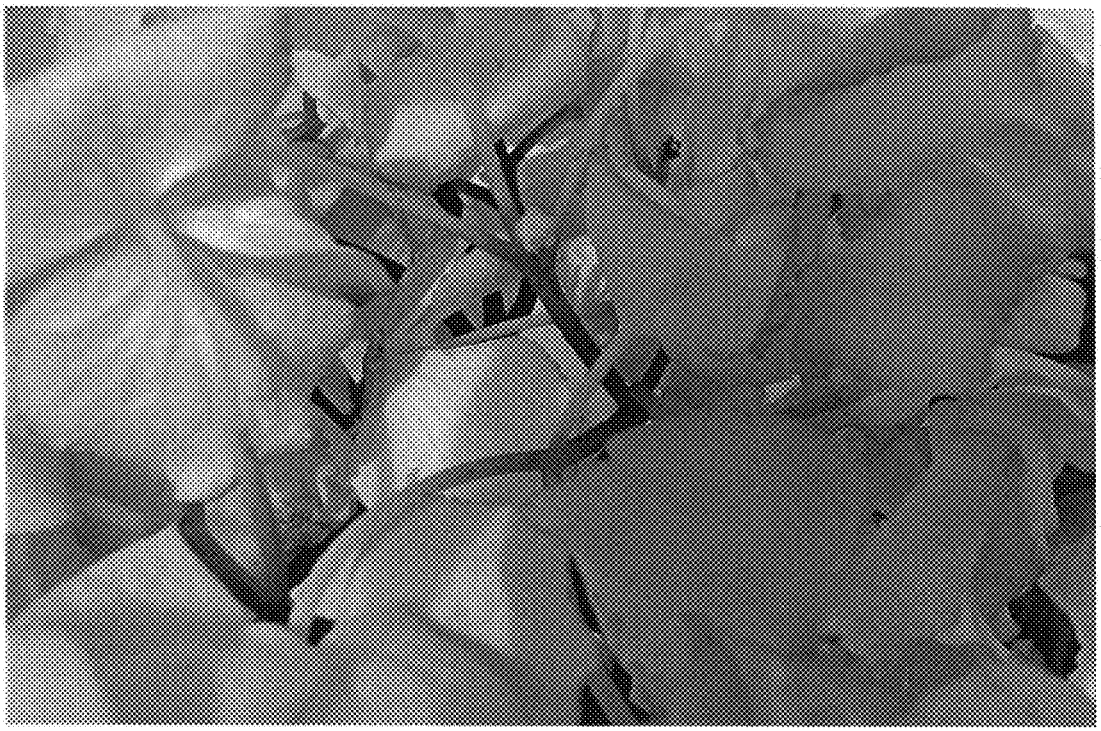
FIG. 5 is a close-up view of the center of a panicle of the new variety, showing sepalous florets and non-sepalous florets.
Figure 6:
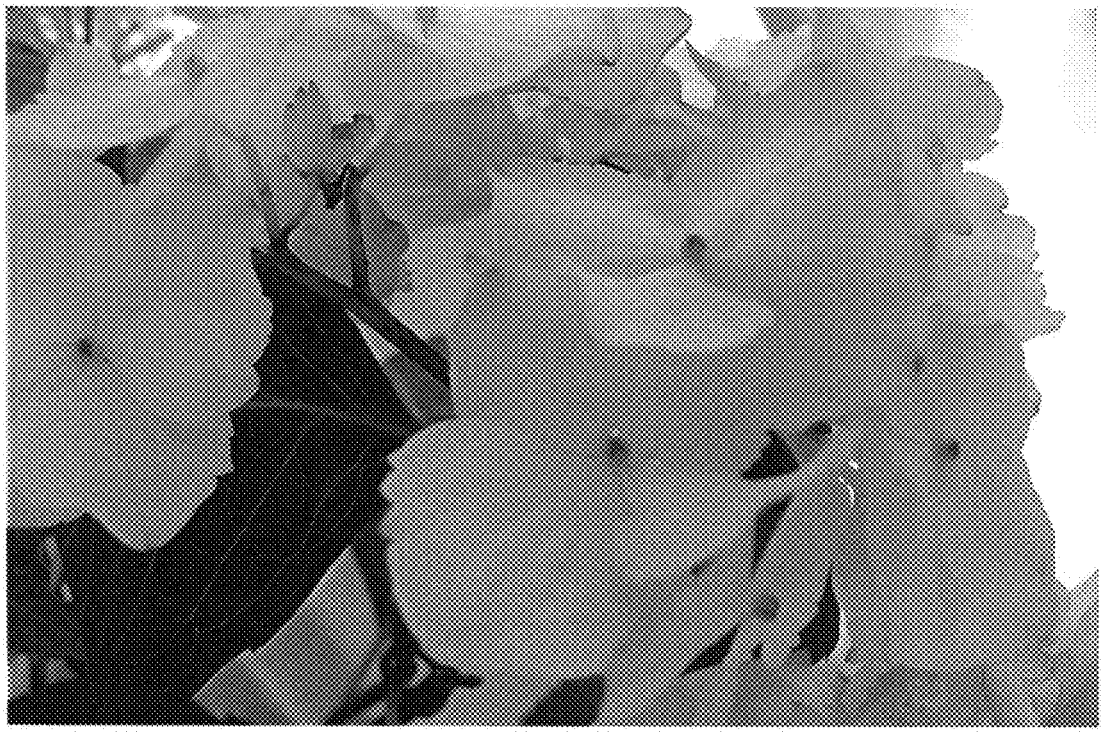
FIG. 6 is a close-up view of sepalous florets of the new variety.
Figure 7:
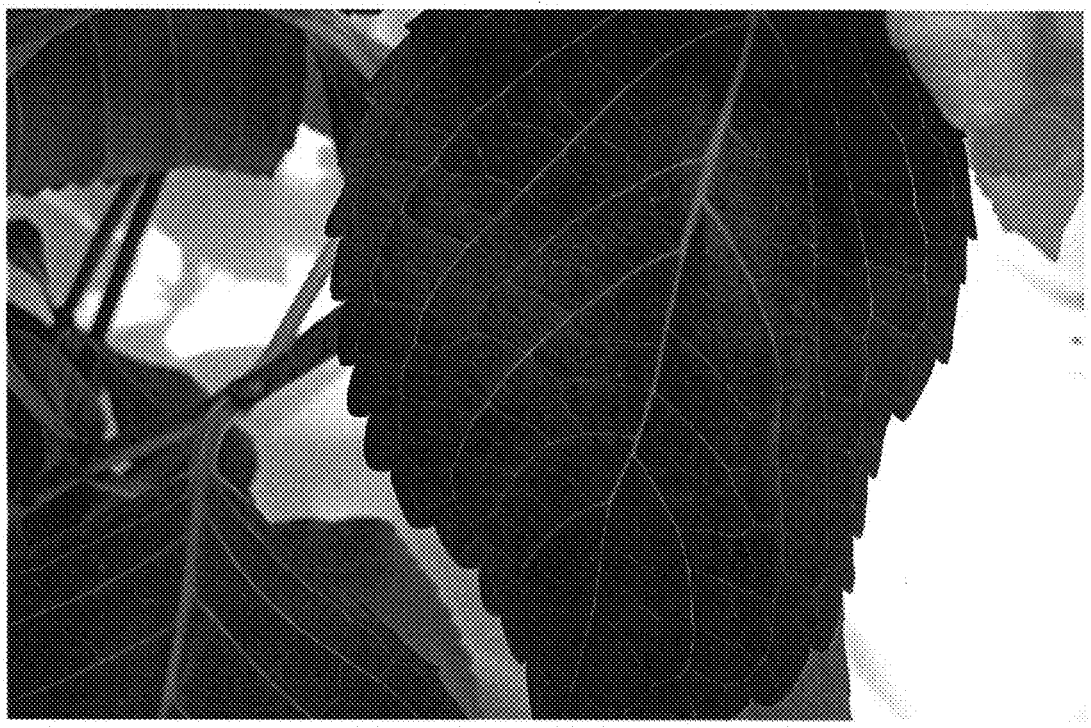
FIG. 7 is a close-up view of the adaxial surface of a mature leaf.

The plants shown in the figures are approximately 50 weeks old. The plant started out as cuttings, taken from the stem of a grown plant. The plant was pinched early to promote lateral branches. Aluminum was not added to the soil of the observed plants. The plant shown is underwatered, but revived after water was added.

The new variety has not been observed under all possible environmental conditions. The phenotype may vary significantly with variations in environment such as temperature, light intensity and day length. Color determinations were made with The Royal Horticultural Society (R.H.S.) Colour Chart, in association with the Flower Council of Holland, located in Lieden.

THE PLANT

Origin: Controlled cross. The new cultivar originated as a seedling from a controlled cross between the unpatented variety known as 'Sabrina' which was the seed parent and the patented variety 'Glory' which was the pollen parent.

Form: Upright, compact shrub. A typical plant with a mature inflorescence that is ready for sale is approximately 17" high (with stakes) and has a diameter of 20" when grown in a 6" pot with appropriate soil amendments. The pictured plant had seven stems with one inflorescence per stem with 1 cutting per pot.

Growth: Upright, vigorous growth habit. Inflorescence is large. The plant branches easily with shoots forming at the base of the plant. Lateral branches are similar in appearance and form to the main stems.

Stems: Lenticels are present. Lenticels are R.H.S. 86 A (violet group) and are 1 to 4 mm long. The surface of young stems is glabrous. Stems become woody as they age. The color of typical young stems and young lateral branches is R.H.S. 144 A (green group). The older portions of the stems are R.H.S. 199 A (grey-brown group) Younger portions of the stems are 5 to 6 mm in diameter. Older portions of the stems are 5 to 6 mm in diameter.

Foliage: Abundant. Leaves are opposite on stem and lateral branches.

*Shape of leaf.*—Elliptic with acute base and apex. Margins are serrate.

*Texture.*—Glabrous; veins dominate on the underside of the leaf and are sunken on the upper leaf surface.

*Color.*—Mature leaves have an upper side that is R.H.S. 147 A (yellow-green group), and an under side that is R.H.S. 138 A (green group). Leaves are pinnately veined. The midvein and veins branching off the midvein are large and prominent on the underside of the leaves. Veins are R.H.S. 138 B (green group). Leaves are as wide as 11 cm and 16 cm long. Petioles are smooth and 4-5 cm long and 4 mm wide. Petioles are R.H.S. 138 A (green group).

BUDS

Form: Globose with 4 to 5 connate, elliptic, smooth petals. Most buds, whether they will mature into sepalous or non-sepalous florets, have 4 petals. Buds in the center of the inflorescence are non-sepalous. The majority of buds will develop into sepalous florets. Buds can be 3 mm in diameter and still unopened.

Aspect: Smooth.

Arrangement: Borne on branched panicles.

INFLORESCENCE

Form: Paniculate. Terminal. As many as 100 [[or more]] individual flowers (florets) per inflorescence. Both sepalous florets and non-sepalous florets borne on same panicle. Flowers do not produce a fragrance. The peduncle [[or panicle]] for the inflorescence is strong and upright. Very few non-sepalous florets developing early on cymes that are later hidden by sepalous florets. Florets, both sepalous and non-sepalous, have anthers and style. Inflorescences are long-lasting, up to six weeks.

Size of inflorescence: Large and globose. Individual inflorescence size is dependent on the number of florets. A typical inflorescence can grow as large as 9" in diameter and be 5" high.

Shape: Clusters of numerous small florets; sepalous florets overlap one another. Sepals are persistent.

Appearance: Showy.

FLORETS

General: The non-sepalous florets at the center of the inflorescence open first. Sepalous and non-sepalous florets are perfect and complete.

*Corolla.*—Generally, for both sepalous and non-sepalous florets there are 4 petals which fall off as flower matures. Petals are typically 4 mm long and 3 mm wide. Pedicel length for non-sepalous florets averages 4 mm. Pedicel length of sepalous florets is between 30 and 40 mm in length for plants of this age. Pedicels of both sepalous and non-sepalous florets continue to elongate as the inflorescence ages. Lenticels are present on pedicels of both sepalous and non-sepalous florets, lenticels are no more than 1 mm long. Lenticels are R.H.S. 59 B (red-purple group). Base of the pedicel is R.H.S. 64 A (red-purple group), remainder is R.H.S. 155 C (white group). Petals of both sepalous and non-sepalous florets are R.H.S. 155 C (white group) with tips that are R.H.S. 74 A (red-purple group). Petals typically fall off with the reproductive organs.

Stamens: 10 stamens. Pollen is R.H.S. 155 C (white group). Plant produces abundant pollen. Filament is approximately 1 mm long. Filament is R.H.S. 155 C (white Group). Anther is 1 mm long and is regular and basally attached.

Stigma: Two to three style. Each style has one stigma. Style is typically 1 mm long. Style is R.H.S. 155 C (white group). Stigma is R.H.S. 155 C (white group).

Ovary: Ovary is partially inferior.

Sepalous florets:

*General.*—Veins dominate on the underside of the sepals.

*Number of sepals.*—4 or 5 sepals per floret, usually 4.

*Aspect of sepals.*—Smooth and glaucescent.

*Shape of sepals.*—Reniform with acuminate apex. Edges are entire, but with some crenation.

*Size of sepals.*—As the florets mature, the sepals enlarge and overlap each other more and more, until, often, there is no space between the sepals when the petals of the florets open. Sepals at maturity are typically 3.0 cm long and 3.0 cm wide. Flowers are typically 5 cm in diameter. The pigmentation of the uppersides and undersides of the sepals are the same: predominantly R.H.S. 155 C (white group) with edges of R.H.S. 63 A (red-purple group).

Fruit: None.

Disease and pest resistance: Unknown.

I claim:

1. A new and distinct *Hydrangea macrophylla* plant named 'BC9.2' substantially as herein shown and described.

* * * * *